(12) United States Patent  
Starkey

(10) Patent No.: US 6,752,338 B2  
(45) Date of Patent: Jun. 22, 2004

(54) BALL MILL

(75) Inventor: John Starkey, Oakville (CA)

(73) Assignee: Starkey & Associates Grinding Design and Process Engineering, Ontario (CA)

( * ) Notice: Subject to any disclaimer, the term of this patent is extended or adjusted under 35 U.S.C. 154(b) by 0 days.

(21) Appl. No.: 10/159,948

(22) Filed: May 31, 2002

(65) Prior Publication Data

US 2003/0038198 A1 Feb. 27, 2003

Related U.S. Application Data

(60) Provisional application No. 60/294,860, filed on May 31, 2001.

(51) Int. Cl.[7] ............................................. B02C 17/02
(52) U.S. Cl. .................. 241/30; 241/172; 241/179; 241/183; 241/184
(58) Field of Search ..................... 241/71, 72, 82.1, 241/82.3, 171, 172, 176, 179, 182, 183, 184, 24.24, 24.25, 24.31, 30

(56) References Cited

U.S. PATENT DOCUMENTS

| | | | | |
|---|---|---|---|---|
| 1,872,036 A | * | 8/1932 | Hardinge | ..................... 241/70 |
| 2,911,160 A | * | 11/1959 | Hartwig | ..................... 241/175 |
| 4,200,242 A | * | 4/1980 | Ueda | ..................... 241/183 |
| 4,744,525 A | * | 5/1988 | Ortega De La Orden | ... 241/171 |
| 5,390,866 A | * | 2/1995 | Kochnev et al. | ............ 241/181 |

* cited by examiner

Primary Examiner—Allen Ostrager  
Assistant Examiner—Jimmy T Nguyen  
(74) Attorney, Agent, or Firm—Ohlandt, Greeley, Ruggiero & Perle

(57) ABSTRACT

A pilot plant scale SAG mill suitable for use in design of a commercial scale SAG mill. The ball mill has a cylindrical outer chamber having flanges at opposed ends. The cylindrical outer chamber contains a removable grinding chamber in the form of a sleeve. The removable grinding chamber has a diameter of 2–5 feet and a ratio of diameter:length in the range of 3:1 to 1:1. The removable grinding chamber contains a plurality of steel balls. The removable grinding chamber extends partly down the length of the cylindrical chamber and has longitudinal lifters attached to the internal surface of the sleeve. The lifters are capable of lifting steel balls located in the removable grinding chamber during rotation of the cylindrical outer chamber. The removable grinding chamber has means at one end for receiving particulate ore from a feed hopper and a removable diaphragm at the opposed end, the removable diaphragm having outlet ports therein for discharge of ground particulate ore into the cylindrical outer chamber. The cylindrical outer chamber has discharge ports for discharge of ground particulate from the SAG mill, and means to rotate the cylindrical chamber about a longitudinal axis.

7 Claims, 4 Drawing Sheets

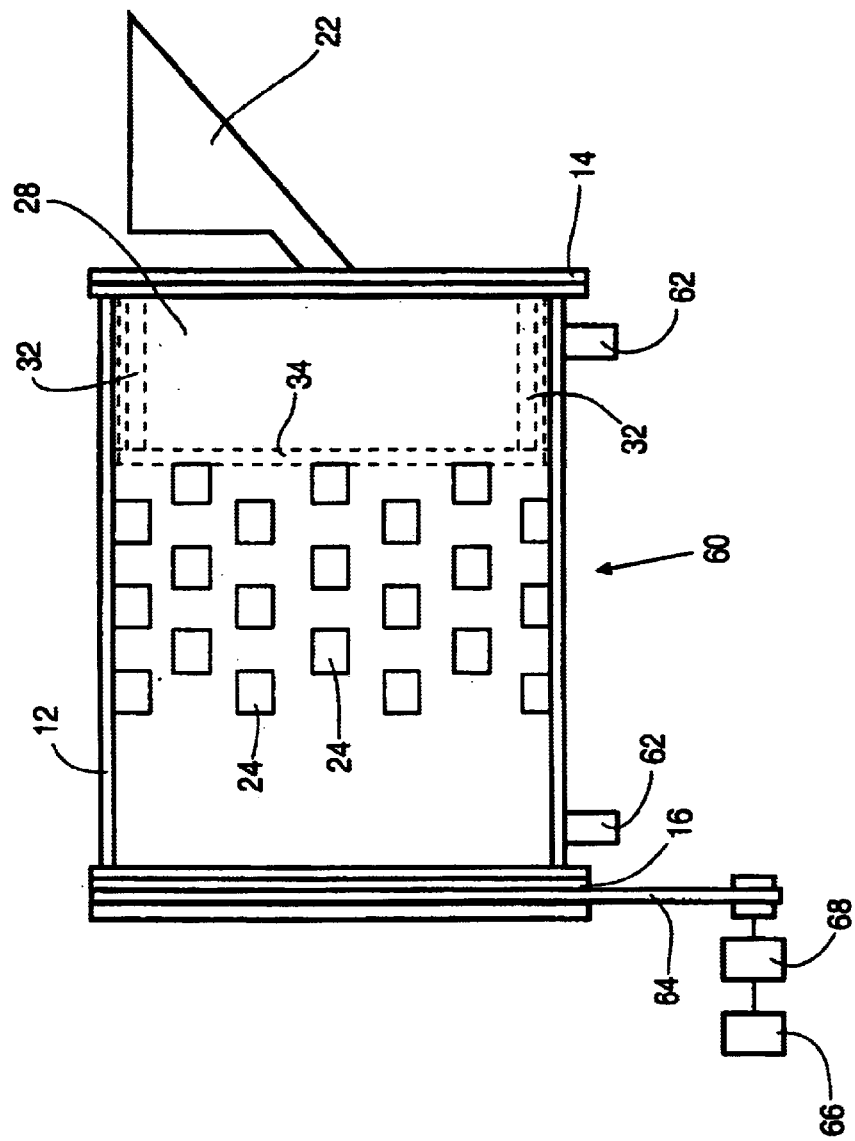

BALL MILL

CROSS-REFERENCE TO RELATED APPLICATION

The present application is claiming priority of U.S. Provisional Patent Application Serial No. 60/294,860, which was filed on May 31, 2001.

FIELD OF THE INVENTION

The present invention relates to a ball mill. The ball mill is used to effect a reduction in the size of ore particulate, especially samples of ore obtained from an ore body. In particular, the present invention relates to a ball mill that is capable of milling small samples of ore continuously in a manner that provides information that is usable for the design of a large commercial scale ball mills, and to do so with smaller sample sizes than currently utilized in the industry. The ball mill also provides representative samples of ore suitable for further testing e.g. studies of leaching and concentration of the ore. The ball mill of the present invention will be referred to herein as a semi-autogenous grinding (SAG) mill, to distinguish over ball mills known in the art.

BACKGROUND TO THE INVENTION

Ore that is mined from the ground, whether in a surface mine or from underground, is obtained in a wide variety of sizes of particulate, varying from relatively small sizes to large chunks of mineralized material. The ore must be reduced to a size of particulate that is suitable for leaching or other separation of metal values from the ore.

A variety of techniques are used in the industry to effect size reduction, examples of which include crushing, rod mill and ball mill grinding, autogenous (AG) grinding and SAG milling. In SAG milling, the ore is crushed in a rotating mill that contains balls. An autogenous mill differs from a SAG mill in that it is operated with no steel or other balls. The balls in SAG milling are usually steel balls. As the mill rotates, the balls are lifted and then dropped onto the ore. The impact causes the ore to be crushed, cracked, broken or otherwise formed into smaller particulate. When the particulate reaches the required size for subsequent processing of the ore, the particulate is removed from the ball mill through discharge ports or grates. Selection of the particulate to be discharged and removed from the system is controlled by the size of the discharge grates, and the use of screens or the like. In this manner, the SAG mill may be operated in a substantially continuous manner, although it is necessary to empty the mill from time to time examine the charge for removal of ore that is not being crushed.

Commercial scale SAG mills are large, and process many tons of ore per hour. It is to be understood that the requirements for a SAG mill will differ depending on the characteristics of the particular body of ore that is to be processed. Moreover, the ore will normally not have the same characteristics throughout the body of ore. For instance, the hardness characteristics of the ore and the concentration of metal values are likely to vary. Some parts of the body of ore may be formed of relatively soft rock compared to other parts of the ore body. Consequently, the design of a commercial scale SAG mill needs to be optimized for efficiency in processing of a particular body of ore. Thus, before a commercial scale SAG mill may be designed and constructed, it is necessary to test the milling characteristics of the ore body, which in turn requires testing of samples from different parts of the ore body. The results obtained are used in the design of the commercial scale SAG mill.

A standard procedure in the industry is to utilize a pilot scale SAG mill having a diameter of six feet. Such a pilot scale SAG mill is used to provide data on flow charts for the ore, and grinding characteristics such as specific energy to achieve the required fineness and product size distribution of the ground material that is representative of and can be used in scale up for the design of a commercial scale SAG mill. However, a pilot scale SAG mill having a diameter of about six feet processes about one ton per hour of ore, and each test must be conducted for several hours in order to obtain data needed for scale-up calculations. Thus, a large quantity of ore is required for any test. As any one sample of ore is not characteristic of the entire ore body, it is necessary to obtain and process numerous samples from the ore body, and many tons of each sample are needed.

The alternative used in the industry is to utilize a SAG mill having a diameter of about one foot. A SAG mill of this small size requires a 2 kg sample of the ore that is run as a batch laboratory test, not as a continuous pilot plant test. As substantially less of each sample of ore is needed, the time and effort to obtain and provide numerous samples of the ore body and the time to process the samples in this small size of SAG mill are significantly reduced. However, the one-foot SAG mill only provides data on ore hardness, the projected energy requirements and the amount and size of fines particles that are produced. This is sufficient data for calculations on the scale up of the size of the SAG mill to a commercial size, when enough data is obtained to define the hardness variability function for the body. However, this test does not provide on-line continuous process data that validates the laboratory work and that clients and investors require to prove that the process will work. It also does not provide material that has been ground, grinding being a major contributor to the milling of ore in a commercial scale ball mill. Meaningful pilot plant tests on SAG ball mill ground ore cannot be obtained. In particular, minimal or no data on the grinding aspects of operation of a commercial SAG mill is obtained. Thus, the designer of the commercial scale SAG mill is forced to make assumptions in the calculations, without actual pilot plant support and with no evidence on whether downstream metallurgical processes will respond in the manner predicted from pilot plant work that does not use the proper grinding process.

In North America, the majority if not all of the metallurgical testing is done at a scale of about 100 to 200 kg per hour, with grinding preparation being done on fine crushed ball mill ground ore. By omitting SAG grinding on this material, the opportunity to make serious process selection mistakes is greatly increased, especially when excess SAG generated fines consume large quantities of expensive reagents. The consequence is that a proposed commercial scale SAG mill has not been properly evaluated and that the process being built may be inefficient.

Pilot plant SAG mills with diameters of approximately six-feet have been the test SAG mills accepted and utilized in the industry for about fifty years. However, a more effective apparatus and method for testing samples of an ore body prior to the design of a commercial scale SAG mill and the following processes, is required.

SUMMARY OF THE INVENTION

One aspect of the present invention provides a pilot plant SAG mill comprising a cylindrical outer chamber having flanges at opposed ends, said cylindrical outer chamber having a diameter of 2.5–5.5 feet and a ratio of length to diameter in the range of greater than 1:1, said cylindrical outer chamber containing a removable grinding chamber in the form of a sleeve, longitudinal lifters and a diaphragm, said removable grinding chamber having a ratio of diameter to length in the range of 3:1 to 1:1 and containing a plurality of steel balls not exceeding 15% of the grinding chamber volume, said removable grinding chamber extending partly down the length of the cylindrical outer chamber and having said longitudinal lifters attached to the internal surface of the sleeve, said lifters being capable of lifting steel balls and ore located in the removable grinding chamber during rotation of the cylindrical chambers, said removable grinding chamber having means at one end for receiving particulate ore from a feed hopper and said removable diaphragm at the opposed end, said removable diaphragm having outlet ports therein for discharge of ground particulate ore into the cylindrical outer chamber, said cylindrical outer chamber having discharge ports for discharge of ground particulate from the SAG mill, and a means to rotate the cylindrical outer chamber about a longitudinal axis.

In embodiments, the means to rotate the cylindrical outer chamber is by use of a vari-speed chain or V-belt drive, especially using a pulley or sprocket bolter at the discharge end flange of the cylindrical outer chamber.

Another aspect of the present invention provides a method of testing the milling properties of a particulate ore, comprising:

feeding particulate ore to a pilot plant SAG mill, said SAG mill comprising a cylindrical outer chamber having flanges at opposed ends, said cylindrical outer chamber having a diameter (d) of 2.5–5.5 feet and a ratio of length to diameter in the range of greater than 1:1, said cylindrical outer chamber containing a removable grinding chamber in the form of a sleeve, longitudinal lifters and a diaphragm, said removable grinding chamber having a ratio of diameter to length in the range of 3:1 to 1:1, said removable grinding chamber extending partly down the length of the cylindrical outer chamber and having said longitudinal lifters attached to the internal surface of the sleeve, said lifters being capable of lifting steel balls and ore located in the removable grinding chamber during rotation of the cylindrical chambers, said removable grinding chamber having means at one end for receiving particulate ore from a feed hopper and said removable diaphragm at the opposed end, said removable diaphragm having outlet ports therein for discharge of ground particulate ore into the cylindrical outer chamber, said cylindrical outer chamber having discharge ports for discharge of ground particulate from the SAG mill, and a means to rotate the cylindrical outer chamber about a longitudinal axis, said removable chamber containing a plurality of steel balls having a diameter in the range of 1 to 4 inches, said steel balls occupying not more than 15% of the volume of the removable grinding chamber;

rotating said cylinder about a longitudinal axis at 65–80% of critical speed ($S_c$), said critical speed in rpm being defined as $S_c = 76.63/\sqrt{d}$, where d is the grinding chamber inside diameter in feet and discharging ground particulate ore through said removable diaphragm into said cylindrical grinding chamber, and discharging said ground particulate ore from the cylindrical chamber.

In preferred embodiments of the method, the ground particulate ore is discharged discharge ports e.g. through 5×5 inch discharge ports, in the cylindrical outer chamber, located in sequence in circumferential rows down the length of the cylindrical outer chamber.

BRIEF DESCRIPTION OF THE DRAWINGS

The present invention is illustrated by the embodiments shown in the drawings, in which:

FIG. 6 is a schematic representation of a side view of an embodiment of the SAG mill of the invention.

DETAILED DESCRIPTION OF THE INVENTION

Figure 1:
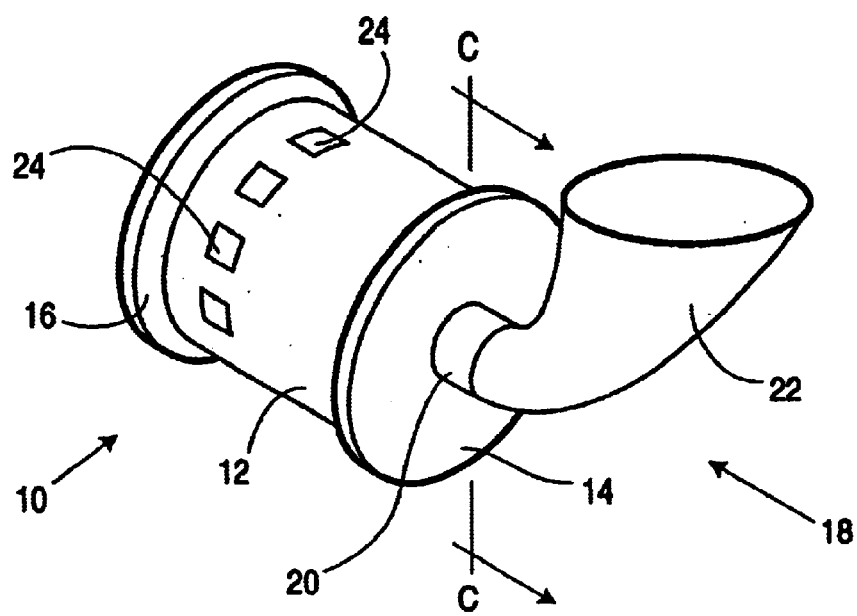
FIG. 1 is a schematic representation of a perspective view of a SAG mill, without discharge chute.

The present invention relates to a SAG mill, and especially to a SAG mill for the milling or grinding of samples of ore on a scale that is suitable for use in design of a commercial scale SAG mill for the grinding of ore. An embodiment of the SAG mill is illustrated in the drawings.

FIG. 1 shows a ball mill, generally indicated by 10. Ball mill 10 has a cylinder 12 that extends between flanges 14 and 16. Flange 16 is a sealed flange i.e. there would normally not be any openings or connections through flange 16. However, flange 14 has the feed section for the ball mill, generally indicated by 18 and shown in greater detail in FIG. 5 below. Feed section 18 has inlet feed 20 and feed hopper 22, both of which are shown in greater detail in FIG. 5. Cylinder 12 has discharge ports 24, of which four are visible in FIG. 1. Any convenient number of discharge ports may be used e.g. 2–10, with 8 being a preferred number of discharge ports.

Discharge ports may be square, rectangular, oval or round or other convenient shape, with a preferred embodiment being square. Discharge ports are located away from flange 14 i.e. the inlet flange, for reasons that will be apparent. In particular, the discharge ports are in the latter half of cylinder 12, as measured from flange 14. In the embodiment illustrated, discharge ports 24 are shown as being circumferentially aligned but the ports may be off-set i.e. in a non-aligned arrangement.

Figure 2:
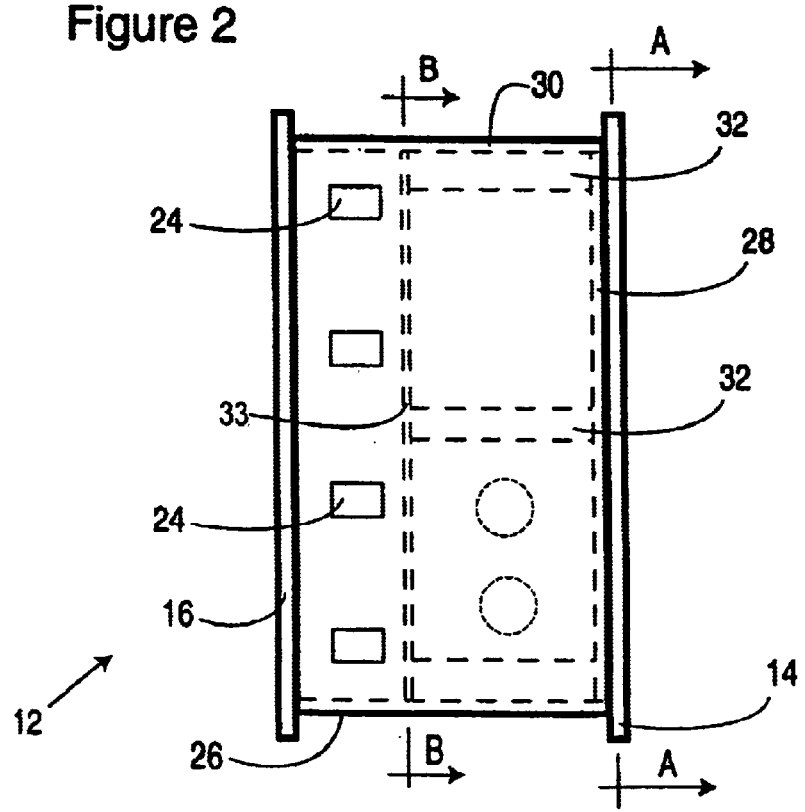
FIG. 2 is a schematic representation of the cylindrical grinding chamber of the SAG mill of FIG. 1, without discharge chute.

FIG. 2 shows cylinder 12 in greater detail, with internal structure being shown. Cylinder 12 has flanges 14 and 16, as well as the plurality of discharge ports 24 discussed above. In addition, cylinder 12 has sleeve 28 inserted therein. Sleeve wall 30 is in free and unrestricted sliding engagement with cylinder wall 26. For instance, the sleeve is preferably about one inch smaller in outside diameter than the inside diameter of cylinder 12. Sleeve 28 extends inwardly in cylinder 12 from flange 14, for a distance that is less than the full length of cylinder 12, for instance about 12 inches less than the full length of cylinder 12.

Sleeve 28 and discharge ports 24 may be located such that discharge ports 24 are in cylinder 12 beyond the end 34 of sleeve 28. Sleeve 28 and discharge ports 24 may also be located at the same longitudinal location i.e. such that sleeve 28 does overlap discharge ports 24. The discharge ports and slots in end 33 discussed below allow inspection of the charge within sleeve 28 during testing. End 33 of sleeve 28 is a diaphragm, which is discussed below.

Sleeve 28 has a plurality of lifters 32, of which three are shown in FIG. 2. The number of lifters in sleeve 28 may be varied e.g. sleeve 28 may have 6–16 lifters, especially at least 6 lifters, with 8 lifters being preferred for a 3 ft. diameter cylindrical grinding chamber. Lifters 32 are in the form of bars that generally extend for the full length of sleeve 28. Lifters 32 are intended to lift steel balls and ore located in sleeve 28 during rotation of cylinder 12, when SAG mill 10 is in use, with the steel balls effecting crushing of particulate ore in sleeve 28. While the use of lifters per se in SAG mills is known, the optimization of the shape and the effects of shape on wear life is the subject of substantial study using computer simulation of the parameters. Computer simulations need to be validated and the cylindrical grinding chamber described herein will allow testing on a pilot plant scale by inserting alternate grinding chambers with varying configurations and shapes of lifters.

Figure 2A:
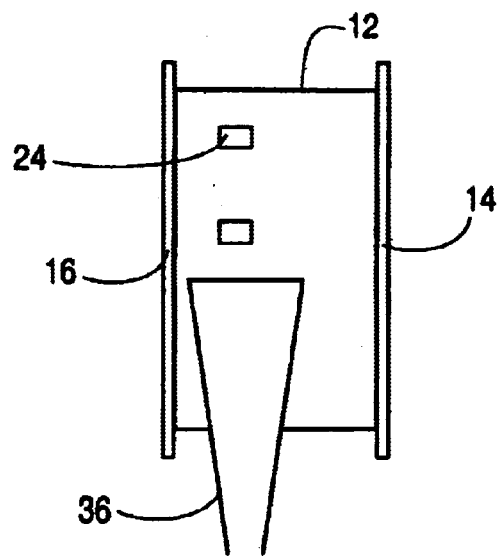
FIG. 2A is a schematic representation of the cylindrical grinding chamber of the SAG mill of FIG. 1, with discharge chute.

FIG. 2A shows cylinder 12 with discharge chute 36. Discharge chute 36 is located to collect ground particulate ore passing out of discharge ports 24 on rotation of cylinder 12, for removal of the ground particulate ore from the apparatus. A slurry containment chute may also be used, located partially around cylinder 12 to collect any spillage of ground ore (not shown).

Figure 3:
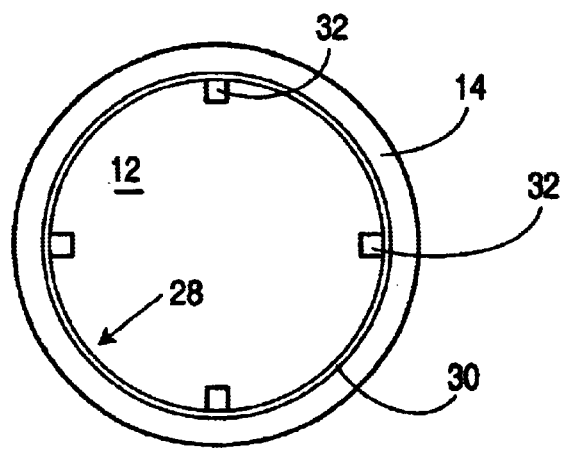
FIG. 3 is a schematic representation of a cross-section of the feed end of the cylindrical grinding chamber, through A—A of FIG. 2.

FIG. 3 shows a cross-section through A—A of FIG. 2, being an end view of cylinder 12. Sleeve 28 has sleeve wall 30 located in cylinder 12. Sleeve wall 30 has a plurality of lifters 32, of which four are shown in FIG. 3.

Figure 4:
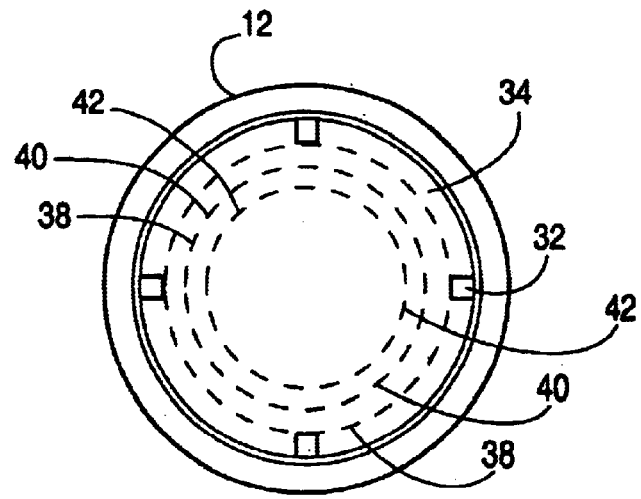
FIG. 4 is a schematic representation of the diaphragm attached to the sleeve of the ball mill, through B—B of FIG. 2.

FIG. 4 shows a cross-section through B—B of FIG. 2, being diaphragm 34 in cylinder 12. Diaphragm 34 is attached to lifters 32, being the opposed ends of lifters 32 to those shown in FIG. 3. In addition, diaphragm 34 has a plurality of slots, 38, 40 and 42, which are arranged annularly in three or more separate annular row arrangements. While slots 38, 40 and 42 are convenient arranged annularly, and preferred in such an array, it is understood that slots 38, 40 and 42 may be in any other pattern, including a random pattern. Slots 38, 40 and 42 are for discharge of ground particulate ore from sleeve 28 into cylinder 12 from which the ground particulate ore is discharged through discharge ports 24 into discharge chute 36. Diaphragm 34 would normally be of a slightly greater diameter than sleeve 28, to maintain sleeve 28 in a stable position during use.

It is understood that the size of the slots will determine the maximum size of particulate discharged from the SAG mill. Thus, the size of the slots may be varied depending on the requirements for the SAG mill, with very small slots e.g. narrower than ¼ inch, being prone to plugging during use. Slot widths can vary from ¼ inch to a maximum of 4 inches, depending on the application and the diameter of the cylindrical grinding chamber being used.

Sleeve 28, with lifters 32 and diaphragm 34 forms a cylindrical grinding chamber.

Figure 5:
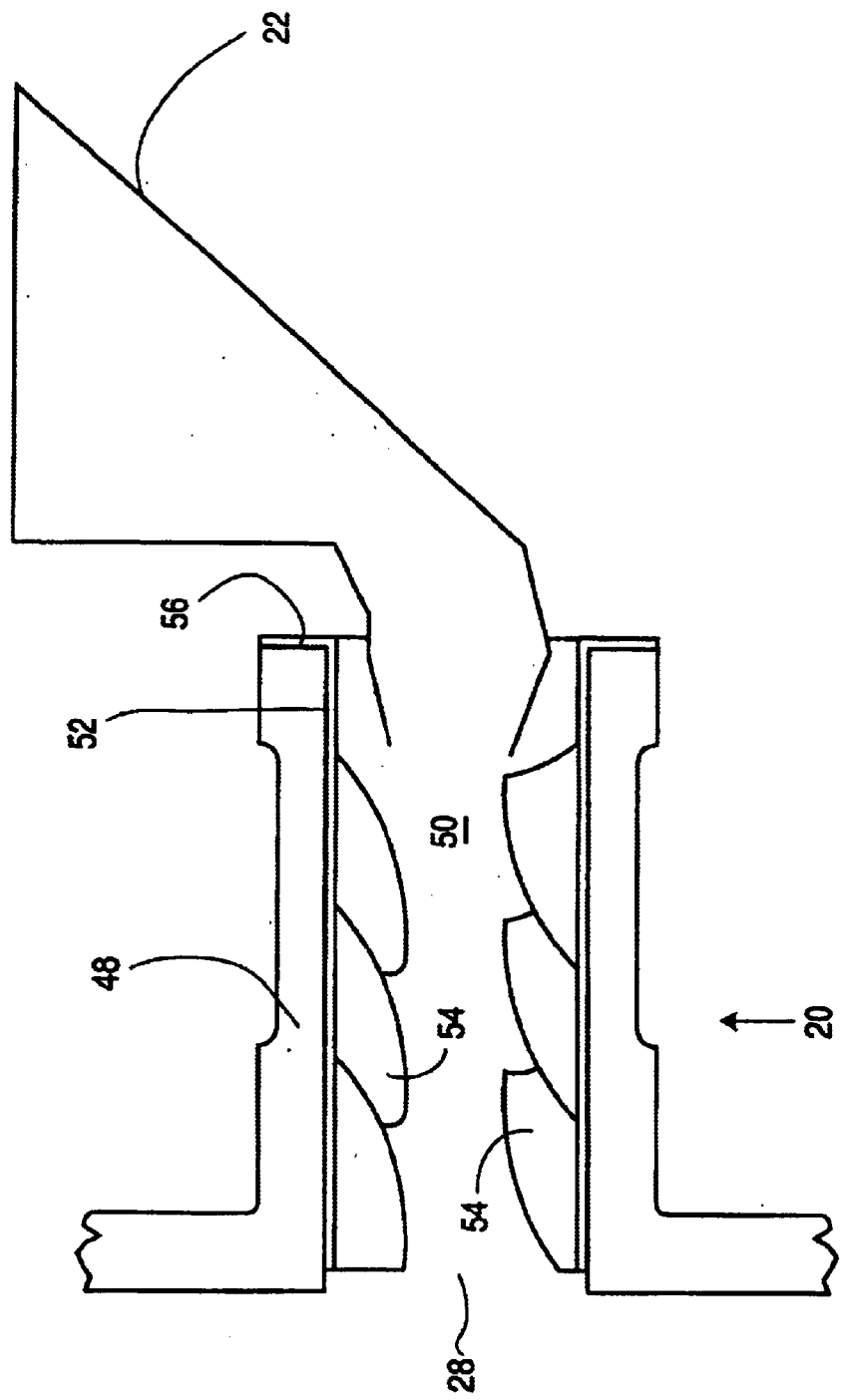
FIG. 5 is a schematic representation of a cross-section of the feed section of the ball mill, through C—C of FIG. 1.

FIG. 5 shows a cross-section of the feed trunnion of the SAG mill, for an embodiment of the invention in which a trunnion mounted SAG mill 48 is used. In the embodiment illustrated, funnel-shaped feed hopper 22 feeds pipe 50. Pipe 50 is part of inlet feed 20. Pipe 50 has a helix for the feeding of particulate ore into sleeve 28. A helix is the preferred method of feeding particulate ore in a trunnion-mounted mill. The helix has a flanged slide-in trunnion liner 52 with a continuous welded helical internal flight 54. Internal flight 54 is bolted to feed flange 56 for trunnion 48. In use, trunnion 48 is rotated, whereby ore is fed by means of the helix into sleeve 28 for grinding by the rotation of the SAG mill.

FIG. 6 shows a side view of an embodiment of the SAG mill of the present invention. SAG mill 60 has cylinder 12 extending between flanges 14 and 16. Feed hopper 22 is connected to flange 14. In this embodiment, feed hopper 22 connects directly into sleeve 28, and is mounted in a manner that permits rotation of cylinder 12. Sleeve 28, lifters 32 and diaphragm form the cylindrical grinding chamber. Sleeve 28 extends only partly down cylinder 12. Cylinder 12 is shown with a plurality of rows of discharge ports 24 that extend around cylinder 12. Cylinder 12 is supported by rollers 62, of which there would normally be two at each end of cylinder 12. Cylinder 12 is driven by V-belt (or chain) 64, which in turn is driven by variable speed motor 66 through gear reducer 68.

In use, ore samples are obtained from a mine. The SAG mill of the invention may be used to evaluate ore samples from a mine site that is not in operation and prior to design of a commercial scale ball mill operation. This is one particularly intended purpose of the pilot plant SAG mill. However, the SAG mill may be used for other reasons, for instance on-going evaluation of an ore body of an existing mine. In addition, an important use of the SAG mill is to prepare ground samples of ore for evaluation e.g. downstream testing of the ore, for instance leaching and concentration steps in a process for treatment of an ore. The SAG mill is capable of providing a representative ground sample of the ore body. The advantage of the small SAG mill is that it is capable of providing data for a flow sheet for a grinding operation, based on smaller samples than presently used in the industry. As noted and for reasons discussed above, data obtained from a small e.g. one-foot diameter SAG mill, does not provide acceptable data for scale up to a commercial operation. For instance, such a small SAG mill does not provide sufficient information on the grinding on the particulate ore, as opposed to crushing of the ore with the steel balls.

The ore samples obtained from an ore body are crushed to a particulate size of 100% passing a three inch grid for a three ft. diameter SAG mill, and proportionally coarser or finer for alternate sizes of SAG mills. The particulate ore is fed to the SAG mill of the invention. The SAG mill is filled with steel balls to a volume of up to 15% of the volume of the cylindrical grinding chamber. Typically, the size of the balls may be varied from 1 to 4 inches in diameter and the quality of the balls may be any kind of steel. However, effects of the size and material from which the balls are formed may readily be carried out using the SAG mill of the invention.

The SAG mill is located on a roller support system, for example as shown in FIG. 6, so that the SAG mill is rotated about the longitudinal axis of the cylinder. The feed system, e.g. a helix feeder as described above or a straight pipe, effects continuous feed of particulate ore into the cylindrical grinding chamber. Use of a sleeve as part of the grinding chamber is important, as it allows the evaluation of various materials of construction for the commercial SAG mill that is to be designed and the evaluation of alternate lifter shapes both for wear minimization, and maximization of throughput of ore. The cylinder is rotated about its longitudinal axis at a speed that is related to the diameter of the SAG mill, according to the formula $S_c = 76.63/\sqrt{d}$, where d is the inside diameter of the grinding chamber in feet, where critical speed ($S_c$) is in rpm. In particular, the cylinder is rotated about its longitudinal axis at 50–80% of critical speed ($S_c$). In preferred embodiments, the cylinder is rotated at 73–75% of the critical speed.

At such speeds of rotation, especially the preferred speed of rotation, the steel balls are lifted by the lifters and drop onto the toe of the charge of particulate ore at an angle approximately perpendicular to the grinding chamber wall at the point of impact, which is the preferred angle of impact. At lower speeds of rotation, the balls are not carried by the lifters to a height within the cylinder that is sufficiently high to obtain effective impact. At higher speeds, the balls tend to remain on the periphery of the cylinder, by the effects of centrifugal force, and fail to fall and impact ore. The critical speed defined above represents the rotational speed at which the balls would remain on the walls of the sleeve by centrifugal force throughout rotation of the cylinder.

The ground particulate ore is discharged through the slots of the removable diaphragm into the cylinder, when the ground ore is of a size that can pass thought the slots. The ground particulate ore is then discharged from the cylinder and collected, optionally for further testing or for size classification. Size classification may be carried out on a screen, with optional recycle of oversize particulate back to the feed to the SAG mill.

The diameter of the grinding chamber sleeve within the cylinder of the SAG mill is within the range of 2–5 feet, and especially 2.5 to 4 feet. The ratio of diameter to width of the grinding chamber sleeve is in the range 3:1 to 1:1, especially 2.5: to 2.0:1.

There are other potential advantages that will result from the use of the SAG mill of the invention. For instance, it will be possible to explore, quantify and optimize all of the normal operating variables related to the operation of a SAG mill, e.g. speed of rotation, steel load, total mill load, slurry discharge density and size of steel balls, as well as other variables. It will be possible to evaluate alternate flow-sheet configurations with a view to finding the most economical combination of mill dimensions (aspect ratio) and power split ratio between a ball mill and a SAG mill. This could include the ability of a mill to change the grinding chamber length. It will be possible to evaluate the creation of fines in a SAG mill environment and to test the effect of these fines on subsequent downstream processes, from gravity to flotation and/or leaching.

As an example of dimensions of a preferred embodiment, a ball mill having cylinder 12 with a length of 30 inches and a diameter of 36 inches was fabricated. The discharge ports were square, with each side being 4.5 inches. Sleeve 28 was 15 inches in length i.e. 50% of the length of cylinder 12. Forty slots were used, each slot being ⅜ inches in height and 3 inches in length. The slots were arrayed in three concentric circles. The grinding chamber sleeve contained 252 lbs of 2 inch diameter steel balls. The ball mill was used in the grinding of samples of ore, and was able to process 167 to 378 kg per hour of very soft and very fine ore.

With respect to FIG. 5, in an embodiment, a pipe with a diameter in the range of 4 to 8 inches may be used. A helix with an internal flight of about 1.5 inches high with a pitch of 4½ inches between turns may also be used.

What is claimed is:

1. A pilot plant SAG mill comprising:
   a cylindrical outer chamber having flanges at opposed ends, said cylindrical outer chamber having a diameter of 2.5–5.5 feet and a ratio of length to diameter in the range of greater than 1:1, said cylindrical outer chamber containing a removable grinding chamber in the form of a sleeve, longitudinal lifters and a diaphragm, said removable grinding chamber having a ratio of diameter to length in the range of 3:1 to 1:1 and containing a plurality of steel balls not exceeding 15% of the grinding chamber volume, said removable grinding chamber extending partly down the length of the cylindrical outer chamber and having said longitudinal lifters attached to the internal surface of the sleeve, said lifters being capable of lifting steel balls and ore located in the removable grinding chamber during rotation of the cylindrical chambers, said removable grinding chamber having means at one end for receiving particulate ore from a feed hopper and said diaphragm at the opposed end, said diaphragm having outlet ports therein for discharge of ground particulate ore into the cylindrical outer chamber, said cylindrical outer chamber having discharge ports for discharge of ground particulate from the SAG mill, and a means to rotate the cylindrical outer chamber about a longitudinal axis.

2. The SAG mill of claim 1 in which the means to rotate the cylindrical outer chamber is by use of a van-speed chain or V-belt drive.

3. The SAG mill of claim 1 in which the diameter of the cylindrical outer chamber is 2.0 to 5.0 feet.

4. A method of testing the milling properties of a particulate ore, comprising:
   feeding particulate ore to a SAG mill, said SAG mill comprising a cylindrical outer chamber having flanges at opposed ends, said cylindrical outer chamber having a diameter (d) of 2.5–5.5 feet and a ratio of length to diameter in the range of greater than 1:1, said cylindrical outer chamber containing a removable grinding chamber in the form of a sleeve, longitudinal lifters and a diaphragm, said removable grinding chamber having a ratio of diameter to length in the range of 3:1 to 1:1, said removable grinding chamber extending partly down the length of the cylindrical outer chamber and having said longitudinal lifters attached to the internal surface of the sleeve, said lifters being capable of lifting steel balls and ore located in the removable grinding chamber during rotation of the cylindrical chambers, said removable grinding chamber having means at one end for receiving particulate ore from a feed hopper and said diaphragm at the opposed end, said diaphragm having outlet ports therein for discharge of ground particulate ore into the cylindrical outer chamber, said cylindrical outer chamber having discharge ports for discharge of ground particulate from the SAG mill, and a means to rotate the cylindrical outer chamber about a longitudinal axis, said removable chamber containing a plurality of steel balls having a diameter in the range of 1 to 4 inches, said steel balls occupying not more than 15% of the volume of the removable grinding chamber;
   rotating said cylindrical outer chamber about a longitudinal axis at 65–80% of critical speed ($S_c$), said critical speed in rpm being defined as $S_c = 76.63/\sqrt{d}$, where d is the grinding chamber inside diameter in feet, and discharging ground particulate ore through said diaphragm into said cylindrical outer grinding chamber, and discharging said ground particulate ore from the cylindrical outer chamber.

5. The method of claim 4 in which the ground particulate ore is discharged from the discharge ports in the cylindrical outer chamber, wherein the discharge ports located in sequence in circumferential row in the cylindrical outer chamber in a portion of the length of the cylindrical outer member beyond the removable grinding chamber.

6. The method of claim 4 which the cylindrical outer chamber is rotated at 73–75% of critical speed.

7. The method of claim 4, in which the diameter of the cylindrical outer grinding chamber is 2 to 5 feet.

* * * * *

UNITED STATES PATENT AND TRADEMARK OFFICE
CERTIFICATE OF CORRECTION

PATENT NO. : 6,752,338 B2
DATED : June 22, 2004
INVENTOR(S) : Starkey, John

It is certified that error appears in the above-identified patent and that said Letters Patent is hereby corrected as shown below:

<u>Column 8,</u>
Line 16, please change the term "van-speed" to -- vari-speed --.
Line 54, please change the term "cylindrical outer grinding chamber" to -- cylindrical outer chamber --.
Line 65, please change the term "cylindrical outer grinding chamber" to -- cylindrical outer chamber --.

Signed and Sealed this

Twenty-fourth Day of August, 2004

JON W. DUDAS
*Director of the United States Patent and Trademark Office*